United States Patent
Giloh (10) Patent No.: US 7,354,424 B2
(45) Date of Patent: Apr. 8, 2008

(54) PROTECTIVE GARMENT

(75) Inventor: Tamar Giloh, Salford (GB)

(73) Assignee: TamiCare Ltd. (GB)

( * ) Notice: Subject to any disclaimer, the term of this patent is extended or adjusted under 35 U.S.C. 154(b) by 48 days.

(21) Appl. No.: 10/723,244

(22) Filed: Nov. 26, 2003

(65) Prior Publication Data

US 2004/0153041 A1    Aug. 5, 2004

Related U.S. Application Data

(63) Continuation-in-part of application No. 09/744,779, filed as application No. PCT/IL99/00434 on Aug. 5, 1999, now Pat. No. 6,987,210.

(60) Provisional application No. 60/429,647, filed on Nov. 27, 2002.

(30) Foreign Application Priority Data

Aug. 7, 1998 (IL) .................................. 125695

(51) Int. Cl.
A61F 13/15 (2006.01)
A41B 9/00 (2006.01)

(52) U.S. Cl. .................... 604/385.07; 604/385.03; 604/386; 604/399; 2/73; 2/78.1; 2/78.2; 2/78.3; 2/78.4; 2/400

(58) Field of Classification Search ........... 604/385.07, 604/385.03, 386, 399; 2/73, 78.1–78.4, 400
See application file for complete search history.

(56) References Cited

U.S. PATENT DOCUMENTS

| | | | |
|---|---|---|---|
| 2,796,064 A | 6/1957 | Green et al. ................. 128/288 |
| 3,027,273 A | 3/1962 | Sacks et al. | |
| 3,032,774 A | 5/1962 | Wade | |
| 4,044,769 A | 8/1977 | Papajohn | |
| 4,223,101 A | 9/1980 | Fine et al. | |
| 4,560,381 A | 12/1985 | Southwell | |
| 4,589,876 A | 5/1986 | Van Tilburg | |
| 4,608,715 A * | 9/1986 | Miller et al. ......................... 2/1 |
| 4,662,876 A * | 5/1987 | Wiegner ..................... 604/380 |
| 4,698,847 A | 10/1987 | Yoshihara ........................ 2/69 |
| 4,880,424 A | 11/1989 | Rautenberg | |
| 4,961,418 A | 10/1990 | McLaurin-Smith ......... 128/157 |
| 5,098,419 A | 3/1992 | Gold | |
| 5,149,336 A | 9/1992 | Clarke et al. | |
| 5,342,333 A * | 8/1994 | Tanzer et al. ............... 604/359 |
| 5,411,493 A * | 5/1995 | Rodriguez .................. 604/290 |
| 5,645,884 A | 7/1997 | Harlow et al. | |

(Continued)

FOREIGN PATENT DOCUMENTS

CH    682288    8/1993

(Continued)

Primary Examiner—Jacqueline F. Stephens
(74) Attorney, Agent, or Firm—McDonnell, Boehnen, Hulbert & Berghoff LLP (57) ABSTRACT

The invention provides protective garments that comprise a liquid impermeable garment body having an inner surface with first and second portions, an absorptive device associated with the first portion of the garment body, and fibers affixed to at least a part of the inner surface of the second portion of the garment body. The protective garment may further comprise a connector, and tubing. The tubing can be used for absorbing or draining fluids away from a person's body, or for transmitting fluids to a person's body.

38 Claims, 7 Drawing Sheets

U.S. PATENT DOCUMENTS

| | | | |
|---|---|---|---|
| 5,685,874 A | 11/1997 | Buell et al. | |
| RE35,687 E | 12/1997 | Igaue et al. | |
| 5,758,367 A | 6/1998 | Torrent Lopez et al. | 2/400 |
| 5,800,245 A | 9/1998 | Barbe-Vicuna et al. | 450/57 |
| 5,845,336 A * | 12/1998 | Golde | 2/93 |
| 5,888,118 A | 3/1999 | Kishi | 450/122 |
| 5,921,976 A | 7/1999 | Seymore | 604/385 |
| 5,965,276 A * | 10/1999 | Shlenker et al. | 428/492 |
| 6,060,638 A | 5/2000 | Paul et al. | 604/378 |
| 6,277,104 B1 * | 8/2001 | Lasko et al. | 604/385.01 |
| 6,365,794 B1 | 4/2002 | Dabi et al. | 604/367 |
| 6,502,250 B2 | 1/2003 | Suga et al. | 2/406 |
| 6,987,210 B1 * | 1/2006 | Giloh | 604/373 |
| 2003/0197311 A1 | 10/2003 | Stephenson et al. | |

FOREIGN PATENT DOCUMENTS

| | | |
|---|---|---|
| CN | 1107279 | 8/1995 |
| DE | 187101 | 7/1907 |
| DE | 19704603 | 1/1998 |
| EP | 0 128 531 A2 | 12/1984 |
| EP | 0 327 823 | 8/1992 |
| EP | 0 737 462 A1 | 4/1995 |
| EP | 1 136 050 A1 | 7/2000 |
| GB | 965901 | 8/1964 |
| GB | 1 209 099 | 10/1970 |
| GB | 1 356 465 | 6/1974 |
| GB | 2 074 085 A | 10/1981 |
| JP | 2004-34354 A | 2/2004 |
| WO | WO 92/10119 | 6/1992 |
| WO | WO 96/36248 | 11/1996 |
| WO | WO97/21411 | 6/1997 |
| WO | WO 97/30671 | 8/1998 |
| WO | WO 00/07468 | 2/2000 |
| WO | WO 01/58656 A1 | 8/2001 |

\* cited by examiner

PROTECTIVE GARMENT

CROSS-REFERENCE

This application claims the benefit of U.S. provisional application Ser. No. 60/429,647 filed Nov. 27, 2002 and is a continuation-in-part application of U.S. patent application Ser. No. 09/744,779, filed Jan. 26, 2001, which is a section 371 of International application no. PCT/IL99/00434, filed Aug. 7, 1999, which claims priority from Israeli patent application no. 125695, filed Aug. 7, 1998, the disclosures of which is incorporated herein by reference.

FIELD OF THE INVENTION

The present invention relates to protective garments generally as well as to methods for manufacture thereof.

BACKGROUND OF THE INVENTION

Various types of protective undergarments are known in the patent literature. The following patents and patent applications and the references cited therein are believed to represent the state of the art: U.S. Pat. No. 5,098,419; PCT Published Patent Application WO 96/36248 and European Patent 327,823.

SUMMARY OF THE INVENTION

The present invention seeks to provide a protective garment which is 3D body fitting, body tight, generally lighter and more comfortable than conventional protective garments and which can be manufactured in large quantities at relatively low cost. The protective garment may be worn under other clothing, may be worn in a portion of the body without clothing or may be worn over clothing. As used herein, a "garment" refers to an undergarment or any article to be worn on the body such as a dressing. As used herein, a "dressing" includes, but is not limited to, any covering for a sore or wound or any opening in the body from which a body fluid is excreted or discharged, such as a bandage or nursing pad or any external treatment given through the skin, like pain relievers.

There is thus provided in accordance with one embodiment of the present invention, a protective garment. In one embodiment, the protective garment is a protective undergarment. In another embodiment, the protective garment is a protective dressing. The protective garment may be used in a variety of applications including clothing applications or medical applications. The protective garment may include two portions: (1) a garment body (which may be integrally formed and which may be composed of a liquid impermeable material); and (2) an absorptive device or material (such as a pad) associated with the garment body.

Preferably, the garment body may include a first portion which is formed with multiple perforations to permit passage of perspiration therethrough, and a second portion which may be substantially not perforated, so as to prevent passage of body secretions and medical dressings therethrough.

In accordance with one embodiment of the present invention, the absorptive device or material is associated with the garment body at the second portion.

In one embodiment, the second portion extends beyond the absorptive device or material. In alternate embodiment, the absorptive material or pad may extend beyond the second portion of the garment body.

There is additionally provided in accordance with a preferred embodiment of the present invention a protective garment comprising an integrally formed garment body formed of a liquid impermeable material, the garment body including a first portion which is formed with multiple perforations to permit passage of perspiration therethrough, and a second portion which is substantially not perforated, so as to prevent passage of body secretions and medical dressings therethrough.

Preferably, the liquid impermeable material is a natural elastomer like latex.

Alternatively, the liquid impermeable material is artificial elastomer like silicone rubber or polyurethane.

In accordance with an embodiment of the present invention, the garment body may have a thickness of less than 300 microns.

Preferably, the protective garment also comprises an absorbent device or material associated to the undergarment body.

The protective garment may be a brassiere, underpants, medical dressing or any other suitable garment or medical device.

The protective garment may have fibers affixed to at least part of one surface of the garment body.

In accordance with one embodiment of the present invention, the absorbent device or material includes a portion extending downward from the crotch along the thigh.

There is additionally provided in accordance with a preferred embodiment of the present invention a method of manufacture of protective garments comprising the steps of forming a garment body of a liquid impermeable material, and forming multiple perforations on a first portion of the garment body to permit passage of perspiration therethrough.

Additionally, in accordance with a preferred embodiment of the present invention, the method includes the step of affixing fibers to at least one surface of the undergarment body. For example, cotton fibers may be affixed to at least one surface of the undergarment body.

In an alternate embodiment of the invention, the protective garment may include two portions: (1) a garment body and a connector (which may be integrally formed and which may be composed of a liquid impermeable material); and (2) tubing. The garment body may be worn on any portion of the body. One example of the portion of the body may include a portion of the face. Another example of the portion of the body may include a portion of the arm.

The connector may be integral with the garment body. Or, alternatively, the connector may be separate from, but attached to, the garment body. The connector connects the tubing to the protective garment. Tubing may be used to absorb or drain liquid from or transmit liquid to the body. The garment body may be composed of a liquid impermeable material such as natural and artificial elastomers. Non-limiting examples of synthetic elastomers include polyisobutylene, isobutylene-isoprene copolymer (butyl elastomer), polyvinyl acetate, polyisoprene, polyethylene, vinyl acetate-vinyl laurate copolymers having vinyl laurate contents of about 5% to about 50% by weight of the copolymer, neoprene (polychloroprene), thermoplastic elastomers, nitrile rubber, synthetic latex (which has no proteins), styrenic elastomers, polyurethane, and silicone rubber, and combinations thereof. Non-limiting examples of natural elastomers include natural rubber such as smoked or liquid latex and guayule, and combinations thereof. Further, the garment body may include a portion which is formed with multiple perforations to permit passage of perspiration therethrough.

The connector may be composed of a shape-retaining material, such as metal, plastic, a composite (e.g. of metal and plastic), or any other suitable material. Non-limiting examples of plastic include polyurethane, polyacrylamide, and polyvinyl chloride (PVC). The connector may have associated with it a material (for example, an absorbent material). The connector may fit with the tubing via a variety of ways, such as by a press fit, by threading on the connector, the tubing or both the connector and the tubing.

A protective garment of the invention can also comprise colors (e.g. pigments or dyes) and/or fragrances (e.g. perfumes) in the liquid impermeable material and/or fibers. A color or fragrance can be added, for example, to an elastomeric emulsion before immersing a mold (which will give the protective garment its shape) into the emulsion. Furthermore, a protective garment of the invention can comprise embossed designs or patterns. The designs or patterns can be created by engraving a design in the garment mold. For example, if the protective garment is to be used by children, a teddy bear design can be created in the mold, thereby giving the garment a more attractive appearance to the user. Furthermore, the design can be created with different thicknesses within the same garment (e.g., by further dipping of the desired areas in the liquid latex (either pre- or post-vulcanized) or a synthetic elastomer precursor solution, or by applying coagulants on the mold before dipping, on the desired area to get a thicker result.)

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Reference is now made to FIGS. 1A, 1B, 1C, 1D, 1E, 1F, 1G, 1H and 1I are simplified illustrations of a method for producing protective undergarments in accordance with a preferred embodiment of the present invention. The invention is described hereinbelow with reference to FIGS. 1A-1I, with specific reference to underpants, it being appreciated that the invention applies equally to any other suitable garment (undergarment, garment worn over some other garment, or garment worn in conjunction with no other garment).

Figure 1A:
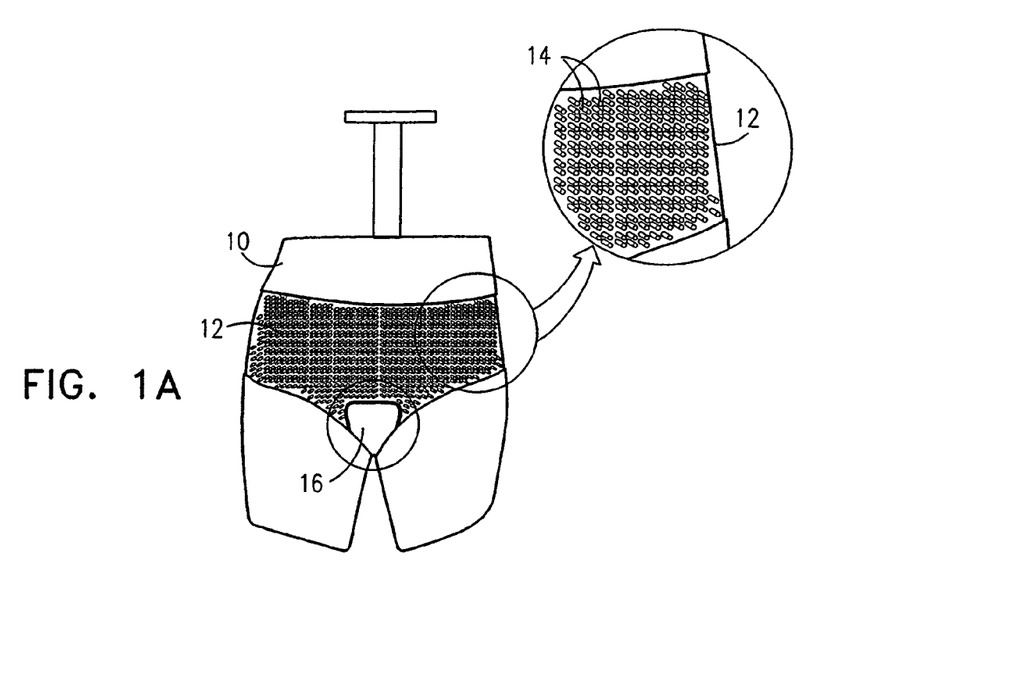
FIGS. 1A, 1B, 1C, 1D, 1E, 1F, 1G, 1H and 1I are illustrations of a method for producing protective garments in accordance with a preferred embodiment of the present invention.

As seen in FIG. 1A, a three dimensional garment form 10 is provided on which an array 12 of protrusions 14, such as needles, is formed in the general shape of underpants to be formed. The protrusions 14 are preferably covered with TEFLON®. The crotch area 16 of the underpants is preferably not formed with protrusions 14. The remained of the form 10 is preferably coated with a non-adhesion substance, such as TEFLON®. Otherwise perforations can be made by mechanical means (e.g., roller press).

Figure 1B:
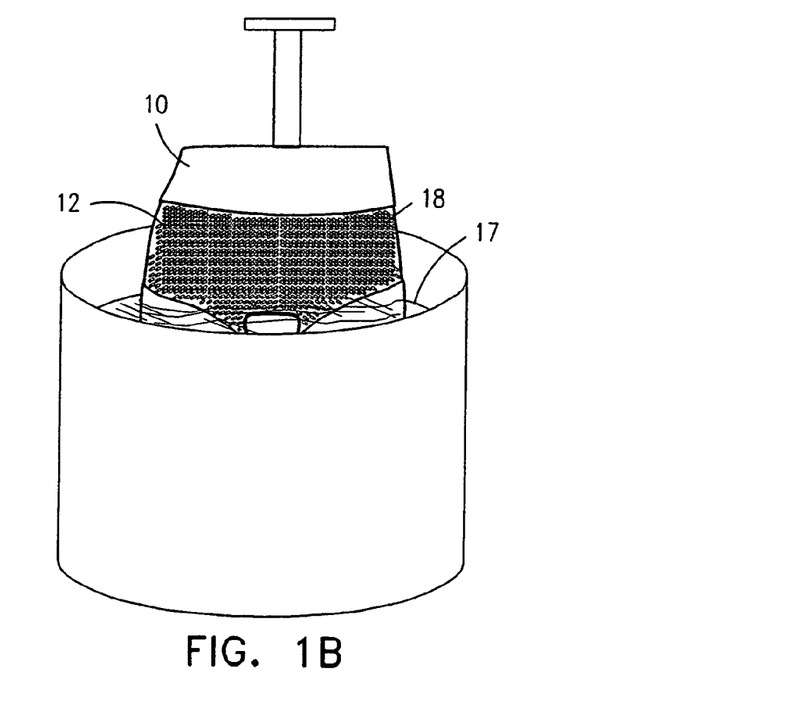

As shown in FIG. 1B, garment form 10 is preferably dipped in a liquid 17, such as latex or silicone, which when allowed to dry, forms a stretchable, light weight garment 18 over array 12 and crotch area 16. It may be appreciated that the provision of protrusions 14 causes the garment 18 to be perforated except at crotch area 16. Thus the garment 18 is "breathable" except at the crotch area 16, where it is liquid impermeable.

Following dipping of garment form 10 into liquid 17, the garment 18 may be rubbed with a mechanical device (not shown) in order to remove any superfluous elastomer material.

Figure 1C:
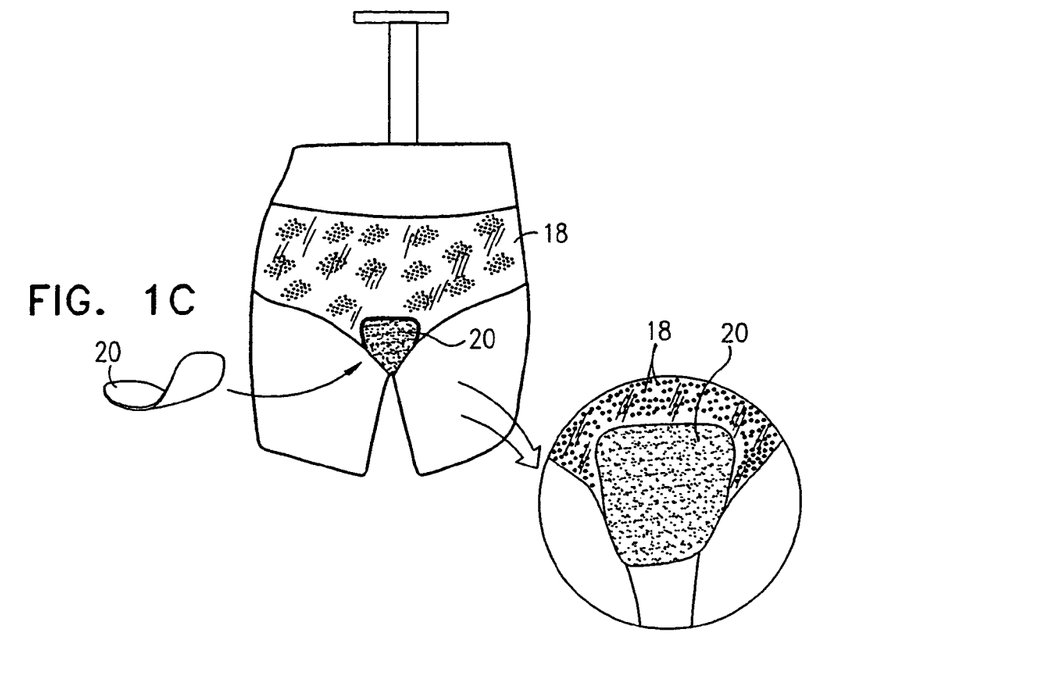

In accordance with a preferred embodiment of the present invention, as illustrated in FIG. 1C, and absorptive pad 20 is associated with the light weight garment 18 at the crotch area 16. However, the absorptive pad 20 can be extended beyond the crotch area if desired. It may be associated by the use of an adhesive or attached to the reminder of garment 18 by virtue of the fact that the latex is allowed to dry on the form 10 in engagement with the absorptive pad 20.

Figure 1D:
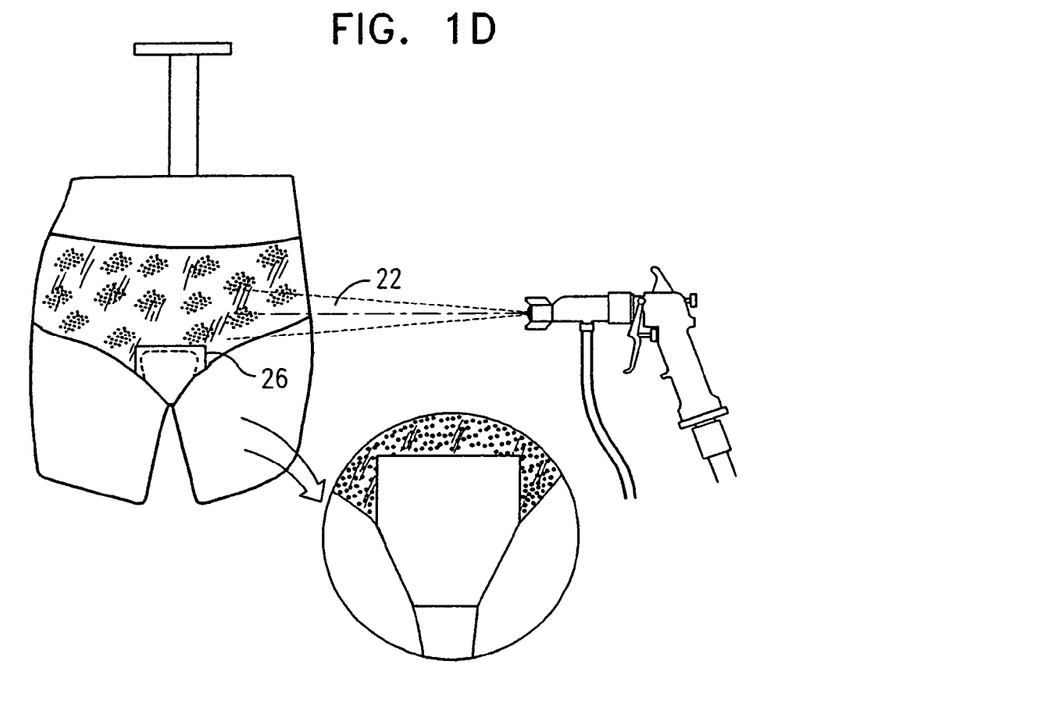
Figure 1E:
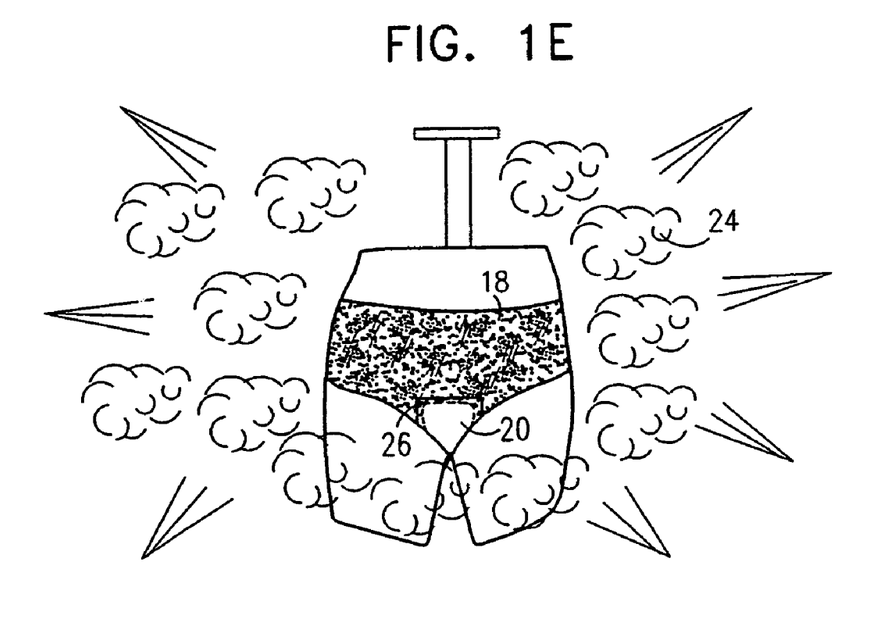

Prior to removal of the garment 18 from the form 10, the exterior surface of the garment on the form 10, which will eventually be turned inside-out to form the interior surface, is preferably sprayed with adhesive 22, as shown in FIG. 1D and thereafter with cotton fibers 24 or any other suitable material as indicated in FIG. 1E, thereby to provide a comfortable and non-stick skin engaging surface. As shown in FIG. 1E, loose fibers 24 are sprayed onto garment form 10 and attach to the exterior surface of the garment 18. Preferably pad 20 is covered during the steps of FIGS. 1D and 1E with a cover 26, which extends somewhat beyond the pad, so as to prevent liquid migration from the pad to the cotton fibers.

Figure 1F:
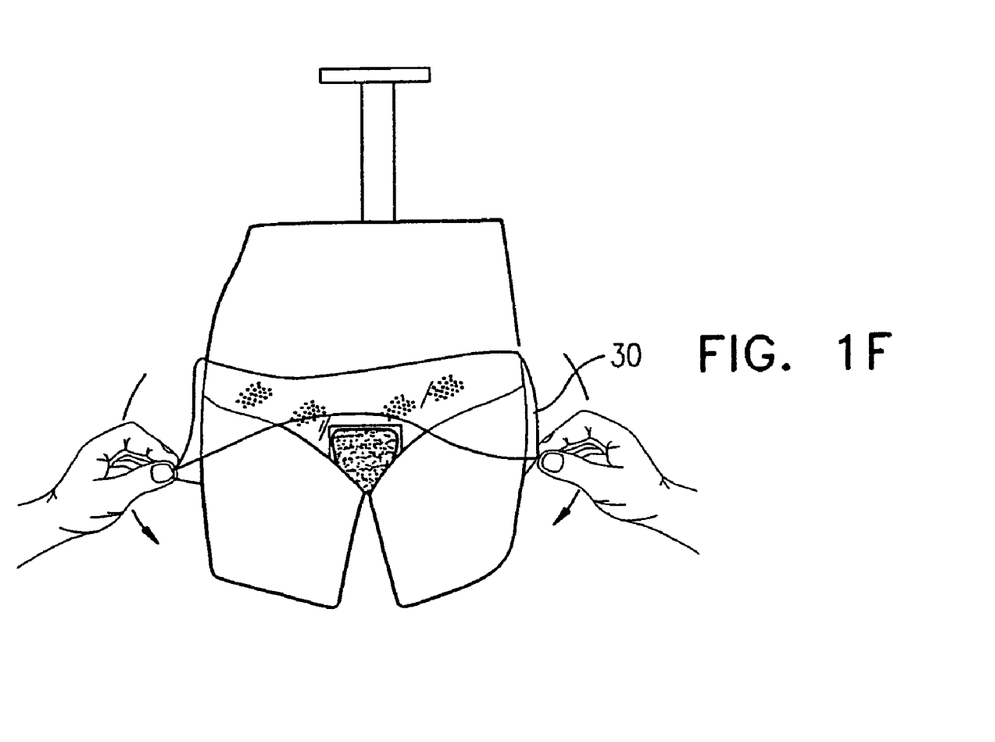

The resulting garment 30 may then be removed from the form 10, as seen in FIG. 1F and turned inside out. The outer surface of garment 30 may be coated or otherwise covered with cotton fiber or any other suitable material and finished in an appropriate manner.

Figures 1G, 1H:
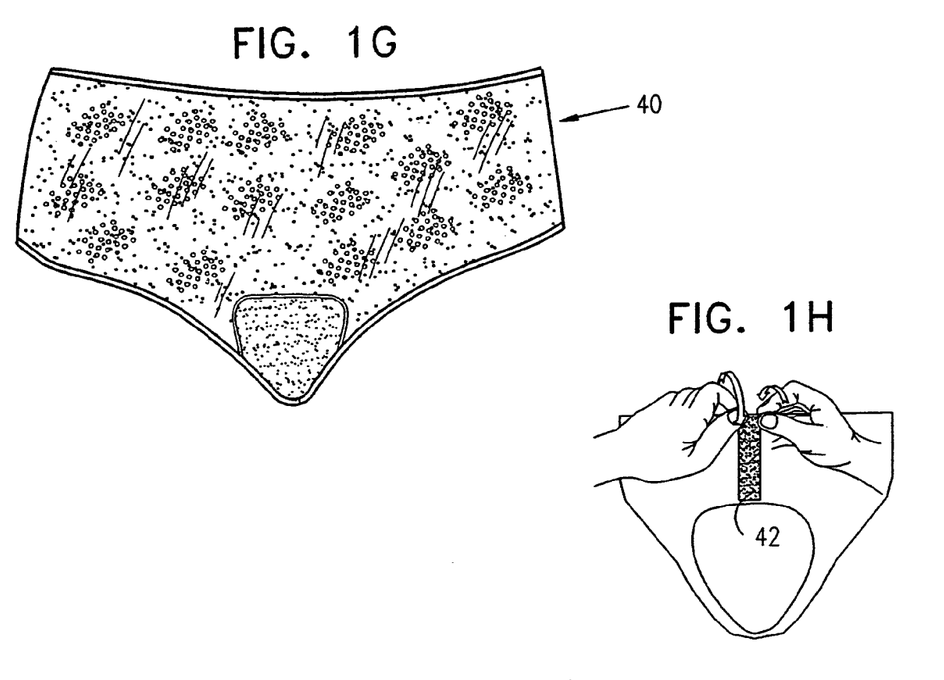
Figure 1I:
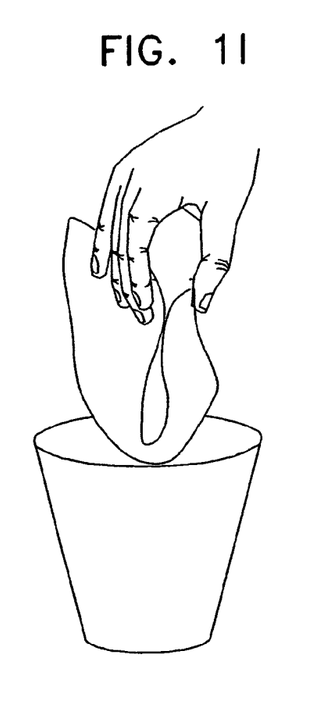

The completed garment 40, as seen in FIG. 1G, is preferably extremely light weight, low cost, stretchable, underpants, which is perforated generally except at the specific areas mostly covered with the absorbent material and which is preferably integrally formed with an internal absorptive pad. The garment is preferably formed of an elastic material, such as latex or silicone, and has a thickness of less than 300 microns. In accordance with a preferred embodiment of the present invention, as seen in FIG. 1H, a tear region 42 may be incorporated in the garment, such as at a side thereof. This enables ease of removal of the garment, by tearing it at region 42. Once removed the torn, worn garment may be disposed of, as illustrated in FIG. 1I.

The final stage of manufacturing of the garment 18 may include a vulcanization process and edge-cutting of the garment, as known in the art.

Figure 2:
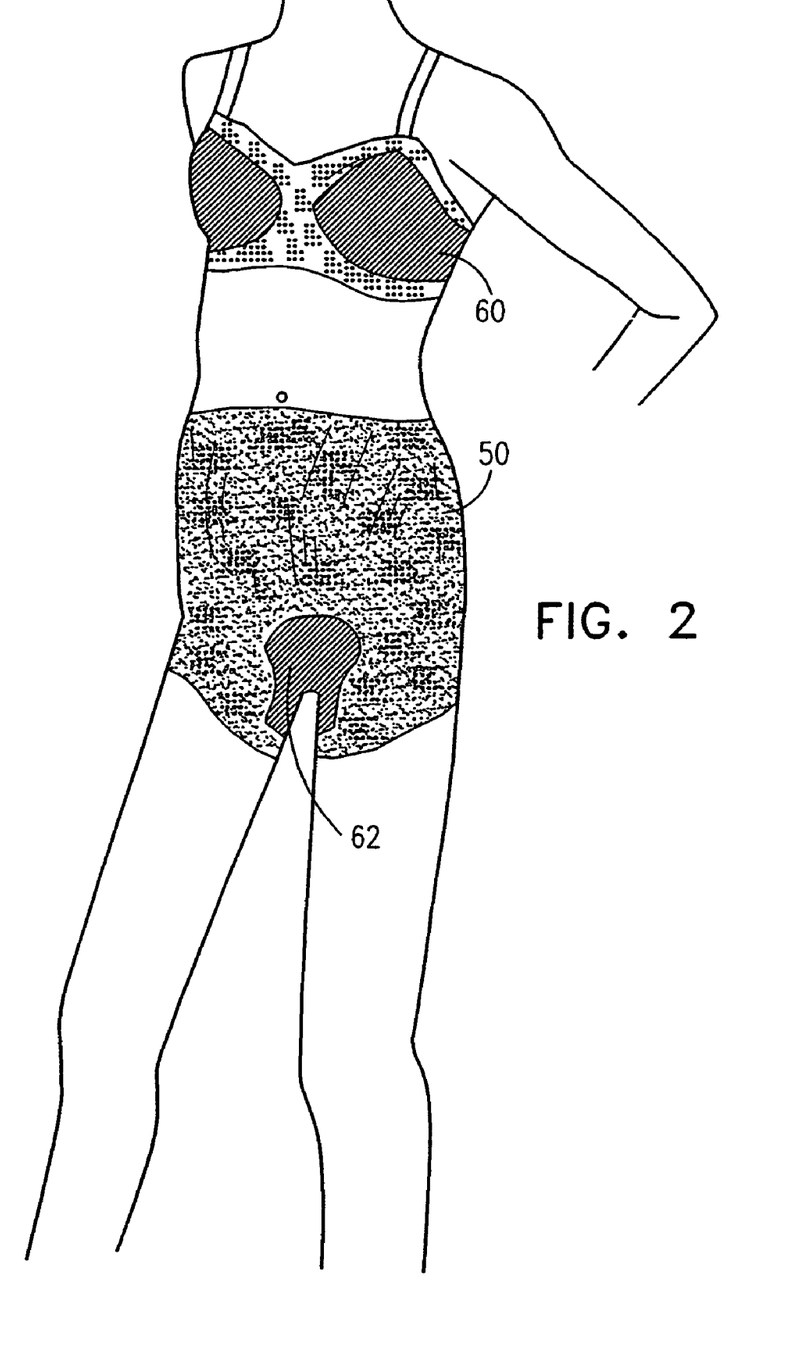
FIG. 2 is a simplified illustration of protective undergarments produced generally by the method of FIGS. 1A-1F in accordance with a preferred embodiment of the present invention.

As can be seen from FIG. 2, the garment may be underpants 50, a brassiere 60, or any other suitable garment. It is noted that the pad 62 of the underpants 50 may have a portion which extend downwardly along the wearer's legs.

Figure 3A:
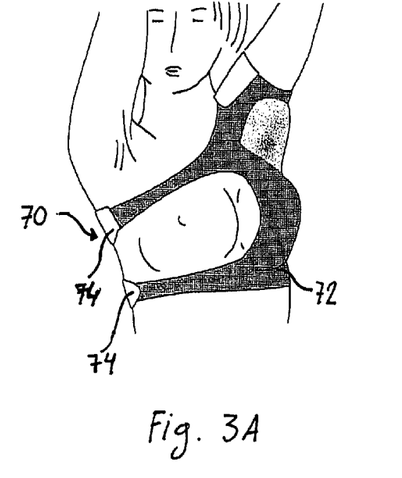
FIG. 3A is a simplified illustration of a medical protective garment.
Figure 3B:
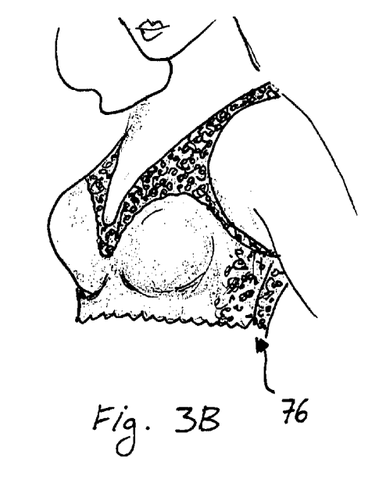
FIG. 3B is a simplified illustration of a sanitary brassiere (for nursing) or medical brassiere (to be used after breast surgery) garments.

Referring to FIG. 3A, there is shown a medical protection garment 70. The medical protection garment may include a garment body 72. A portion of the garment body (or the entire garment body) may be composed of an elastic material or a liquid impermeable material. Examples of materials may include latex or silicone. The garment body 72 may include straps 74 or other types of adjustment devices (such as snaps, clips, fasteners, or the like) in order to adjust the garment body so that it fits snugly or comfortably with the wearer. Some or all of the garment body may be perforated. A portion of the garment body (not shown in the figure) may be covered with material (such as cotton fibers), thereby to provide a comfortable and non-stick skin engaging surface. The medical protection garment 70 shown in FIG. 3A may be used to protect, bandage and treat a portion of the body, such as single breast, after a medical procedure (such as a breast surgery). The absorptive device or material associated with the garment body may include medical ointments, medicine for treatments or diagnostic materials. Referring to FIG. 3B, there is shown an alternate embodiment of the garment 76 showing a simplified illustration of a sanitary brassiere (for nursing when a woman is breast feeding) or medical brassiere (to be used after breast surgery) garments.

Figure 4:
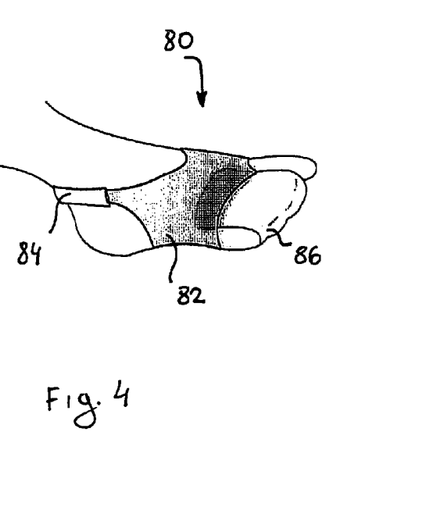
FIG. 4 is a simplified illustration of another medical protective garment.

Referring to FIG. 4, there is shown a simplified illustration of another medical protective garment 80. The medical protective garment 80 may include a garment body 82. A portion of the garment body (or the entire garment body) may be composed of an elastic material or a liquid impermeable material. Examples of materials may include latex or silicone. The garment body 82 may include straps 84 or other types of adjustment devices (such as snaps, clips, fasteners, or the like) in order to adjust the garment body so that it fits snugly or comfortably with the wearer. Some or all of the garment body may be perforated. A portion of the garment body (not shown in the figure) may be covered with material such as cotton fibers, thereby to provide a comfortable and non-stick skin engaging surface. As shown in FIG. 4, an absorptive material 86 is attached to garment body 82 while another portion of material 86 may not be attached to garment body 82. The material 86 may be connected at various portions to the garment body. For example, the material 86 may be attached at two of its ends, one to the upper portion of the garment body 82 and the other to the lower portion of the garment body 82. In this manner, a pocket may be formed. The medical protective garment 80 shown in FIG. 4 may be used on a limb, such as a foot, and may help in the treatment of those who suffer from diabetes.

Figure 5:
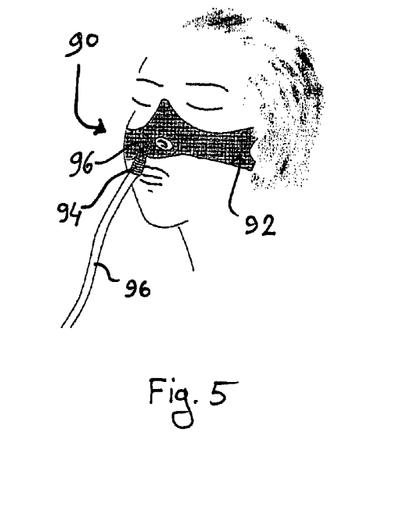
FIG. 5 is a simplified illustration of a medical protective garment with a garment body, a connector and tubing.

Referring to FIG. 5, there is shown a simplified illustration of a medical protective garment 90 with a garment body 92, a connector 94 and tubing 96. The garment body 92 and the connector 94 may be integrally formed. Alternatively, the garment body 92 and the connector 94 may be composed of separate pieces and may be attached to one another (such as by glue, fasteners or the like). The garment body may be composed of an elastic or liquid impermeable material. Similarly, the connector may be composed of an elastic or liquid impermeable material. The garment body 92 may be worn on any portion of the body. One example of the portion of the body may include on a portion of the face, as shown in FIG. 5. Another example of the portion of the body may include a portion of the arm, such as when a user requires Intravenous liquid.

The garment body 92 may include a portion which is formed with multiple perforations to permit passage of perspiration therethrough. Further, the garment body 92 may include straps (not shown) or other types of adjustment devices (such as snaps, clips, fasteners, or the like) in order to adjust the garment body 92 so that it fits snugly or comfortably with the wearer. In the example shown in FIG. 5, the adjustment device may adjust to fit the head of the user.

The connector 94 connects the tubing 96 to the protective garment 90. Tubing 96 may be used to absorb liquid from or transmit liquid to the body. For example, as shown in FIG. 5, the tubing may be used for drainage from the body. Alternatively, tubing may be used to supply fluid or liquid to the body.

The connector may have associated with it a material (for example, an absorbent material). In this manner, the tubing 96 may be connected to the connector 94 with less discomfort to the user. The connector may fit with the tubing via a variety of ways, such as by threading 98. The threading may be on the tubing 96, on the connector 94 or on both the connector 94 and the tubing 96. Alternatively, the tubing 96 may be fit by a press fitting the tubing 96 with the connector 94.

It will be appreciated by persons skilled in the art of that the present invention is not limited by what has been particularly shown and described hereinabove. Rather the scope of the present invention includes variations and modification of the various features described in the specification and shown in the drawings which may occur to a person of ordinary skill in the art upon reading the foregoing description and which are not in the prior art.

What is claimed is:

1. A protective garment comprising:
    an integrally formed garment body of a single layer of stretchable liquid impermeable material having an inner surface, the single layer itself having different thicknesses of the liquid impermeable material within desired areas; and
    loose fibres directly affixed to at least a part of the inner surface of the integrally formed garment body.

2. A protective garment according to claim 1, further comprising an adjustment device associated with the garment body to adjust the protective garment on a wearer.

3. A protective garment according to claim 2, wherein the adjustment device is a strap, snap, clip, or fastener.

4. A protective garment according to claim 1, further comprising a connector associated with the integrally formed garment body; and a tubing connected to the integrally formed garment body by the connector.

5. A protective garment according to claim 4, wherein the connector is associated with an absorptive material.

6. A protective garment according to claim 4, wherein the connector is integrally formed with the garment body.

7. A protective garment according to claim 1, further comprising an absorptive device associated with the inner surface of the integrally formed garment body.

8. A protective garment according to claim 7, wherein the absorptive device is an absorptive material or absorptive pad.

9. A protective garment according to any one of claims 7 or 8, further comprising an adjustment device associated with the garment body to adjust the protective garment on a wearer.

10. A protective garment according to any one of claims 7 or 8, further comprising a connector associated with the integrally formed garment body; and a tubing connected to the integrally formed garment body by the connector.

11. A protective garment according to any one of claims 7 or 8, wherein the surface of the integrally formed garment body has a first portion and a second portion.

12. A protective garment according to claim 11, wherein said first portion of the surface is formed with multiple perforations to permit passage of perspiration therethrough.

13. A protective garment according to any one of claims 7 or 8, wherein the integrally formed garment body has an outer surface, and
further comprising loose fibres directly affixed to at least a part of the outer surface of the integrally formed garment body.

14. A protective garment according to any one of claims 7 or 8, wherein the garment is a body-tight garment.

15. A protective garment according to any one of claims 7 or 8, wherein the garment is a seamless garment.

16. A protective garment according any one of claims 7 or 8, wherein the garment is an undergarment or a dressing.

17. A protective garment according any one of claims 7 or 8, wherein the liquid impermeable material is a natural or synthetic elastomer.

18. A protective garment according any one of claims 7 or 8, wherein the liquid impermeable material and/or the fibers comprise at least one pigment, dye, or a combination thereof.

19. A protective garment according any one of claims 7 or 8, wherein the liquid impermeable material and/or the fibre comprise at least one fragrance.

20. A protective, garment according any one of claims 7 or 8, wherein the garment body has a tear region.

21. A protective garment according any one of claims 7 or 8, wherein the fibres are cotton fibres.

22. A protective garment according to claim 1, wherein the surface of the integrally formed garment body has a first portion and a second portion.

23. A protective garment according to claim 22, wherein said first portion of the surface is formed with multiple perforations to permit passage of perspiration therethrough.

24. A protective garment according to claim 22, wherein an absorptive device is associated with the second portion of the inner surface of the integrally formed garment body.

25. A protective garment according to claim 24, wherein the second portion extends beyond said absorptive device.

26. A protective garment according to claim 24, wherein the absorptive device extends beyond the second portion.

27. A protective garment according to claim 1, wherein the integrally formed garment body has an outer surface, and
further comprising loose fibres directly affixed to at least a pan of the outer surface of the integrally formed garment body.

28. A protective garment according to claim 1, wherein the garment is an undergarment or a dressing.

29. A protective garment according to claim 28, wherein said undergarment is underpants or a brassiere.

30. A protective garment according to claim 28, wherein the dressing is a bandage or dressing pad.

31. A protective garment according to claim 1, wherein the liquid impermeable material is a natural or synthetic elastomer.

32. A protective garment according to claim 1, wherein the liquid impermeable material and/or the fibers comprise at least one pigment, dye, or a combination thereof.

33. A protective garment according to claim 1, wherein the liquid impermeable material and/or the fibre comprise at least one fragrance.

34. A protective garment according to claim 1, further comprising an embossed design or pattern.

35. A protective garment according to claim 1, wherein the garment body has a tear region.

36. A protective garment according to claim 1, wherein the fibres are cotton fibres.

37. A protective garment according to claim 1, wherein the garment is a body-tight garment.

38. A protective garment according to claim 1, wherein the garment is a seamless garment.

* * * * *